United States Patent
Xue (10) Patent No.: US 12,123,927 B2
(45) Date of Patent: Oct. 22, 2024

(54) ALARM DEVICE AND ALARM SYSTEM FOR MRI SYSTEM

(71) Applicant: Siemens Healthcare GmbH, Erlangen (DE)

(72) Inventor: Ting Qiang Xue, Shenzhen (CN)

(73) Assignee: Siemens Healthineers AG, Erlangen (DE)

( * ) Notice: Subject to any disclaimer, the term of this patent is extended or adjusted under 35 U.S.C. 154(b) by 203 days.

(21) Appl. No.: 17/826,438

(22) Filed: May 27, 2022

(65) Prior Publication Data

US 2022/0381856 A1   Dec. 1, 2022

(30) Foreign Application Priority Data

May 27, 2021   (CN) .......................... 202110606399.8

(51) Int. Cl.
| | | |
|---|---|---|
| *G01R 33/28* | (2006.01) | |
| *A61B 5/055* | (2006.01) | |
| *G01H 11/08* | (2006.01) | |
| *G08B 21/18* | (2006.01) | |

(52) U.S. Cl.
CPC ............ *G01R 33/288* (2013.01); *A61B 5/055* (2013.01); *G01H 11/08* (2013.01); *G08B 21/18* (2013.01)

(58) Field of Classification Search
CPC ...... G01R 33/288; A61B 5/055; G01H 11/08; G08B 21/18
See application file for complete search history.

(56) References Cited

U.S. PATENT DOCUMENTS

| | | | |
|---|---|---|---|
| 9,438,981 B2* | 9/2016 | Brown ................ | H04R 5/033 |
| 10,091,578 B2* | 10/2018 | Benner ................ | H04R 3/00 |
| 10,405,823 B1* | 9/2019 | Okutani ............... | A61B 6/107 |
| 10,918,304 B2* | 2/2021 | Wirtz .................. | A61B 5/0051 |
| 2005/0179536 A1* | 8/2005 | Lederer ............... | G08B 7/06 |
| | | | 340/286.07 |
| 2010/0026499 A1* | 2/2010 | Lamb .................. | G16H 40/40 |
| | | | 348/E7.085 |
| 2010/0231483 A1* | 9/2010 | Bazih ................. | G01R 33/283 |
| | | | 382/131 |
| 2012/0268131 A1* | 10/2012 | Assmann ............ | A61B 5/0205 |
| | | | 320/137 |

(Continued)

FOREIGN PATENT DOCUMENTS

| | | |
|---|---|---|
| CN | 201892991 U | 7/2011 |
| CN | 202720735 U | 2/2013 |

(Continued)

*Primary Examiner* — Chico A Foxx
(74) *Attorney, Agent, or Firm* — Banner & Witcoff Ltd.

(57) ABSTRACT

An alarm device for an MRI system may include a body, an operating member, a generator, a power manager and a signal emitter. The operating member may be movably connected to the body. The generator may be connected to the operating member and can convert kinetic energy of motion of the operating member to electrical energy. The power manager may be connected to the generator and can convert electrical energy generated by the generator to an output current. The signal emitter may be connected to the power manager and can use energy obtained from the output current to send a trigger signal wirelessly. Advantageously, the alarm device does not need an external power supply and has a high level of reliability.

16 Claims, 7 Drawing Sheets

(56) References Cited

U.S. PATENT DOCUMENTS

| | | | |
|---|---|---|---|
| 2012/0299443 A1 | 11/2012 | Okabayashi | |
| 2014/0088405 A1* | 3/2014 | Assmann | G16H 50/30 |
| | | | 600/411 |
| 2017/0237368 A1* | 8/2017 | Zhang | H02N 2/18 |
| | | | 310/339 |
| 2018/0172789 A1* | 6/2018 | Sinkus | G01R 33/56358 |
| 2018/0262127 A1* | 9/2018 | Gooneratne | G01V 11/002 |
| 2020/0103479 A1* | 4/2020 | Bollenbeck | G01R 33/385 |
| 2020/0226904 A1* | 7/2020 | Kuang | G08B 21/043 |
| 2021/0116519 A1* | 4/2021 | Weiss | G01R 33/288 |
| 2022/0111201 A1* | 4/2022 | Verzal | G01R 33/02 |
| 2023/0053619 A1* | 2/2023 | Bollenbeck | H04B 1/04 |

FOREIGN PATENT DOCUMENTS

| | | | |
|---|---|---|---|
| CN | 105959499 A | | 9/2016 |
| CN | 107135204 A | | 9/2017 |
| CN | 207743707 U | | 8/2018 |
| CN | 109936303 A | | 6/2019 |
| CN | 210201918 U | | 3/2020 |
| CN | 110946579 A | | 4/2020 |
| CN | 111223486 A | | 6/2020 |
| JP | H11330582 A | | 11/1999 |
| JP | 2012183238 A | | 9/2012 |
| JP | 2020044032 A | * | 3/2020 |
| RU | 124459 U1 | | 1/2013 |
| RU | 130164 U1 | | 7/2013 |

* cited by examiner

ALARM DEVICE AND ALARM SYSTEM FOR MRI SYSTEM

CROSS REFERENCE TO RELATED APPLICATIONS

This patent application claims priority to Chinese Patent Application No. 202110606399.8, filed May 27, 2021, which is incorporated herein by reference in its entirety.

BACKGROUND

Field

The present disclosure relates to an alarm device, in particular an alarm device for an MRI system and an alarm system comprising same.

Related Art

Magnetic resonance imaging (MRI) is a medical imaging technology that can be used to diagnose diseases. When an examination subject is located in a detection region of an MRI system and undergoing examination, in order to make it easy for the examination subject to send an alarm signal to an operator, the MRI system is often provided with an alarm device. Existing alarm devices are mainly realized in the form of squeeze balls; the squeeze ball is connected to an air duct, with the other end of the air duct being connected to a piezoelectric sensor. When the examination subject presses the squeeze ball, the piezoelectric sensor generates an electric signal under the action of air pressure, in order to trigger an alarm. The air duct is easily damaged or subjected to mechanical compression during use, with the result that air pressure cannot be transmitted from the squeeze ball to the piezeoelectric sensor, leading to failure of alarm triggering.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure is to provide an alarm device for an MRI system which has a high level of reliability.

Another object of the present disclosure is to provide an alarm system for an MRI system which has a high level of reliability.

The present disclosure provides an alarm device for an MRI system, comprising a body, an operating member, a generator, a power manager and a signal emitter. The operating member is movably connected to the body. The generator is connected to the operating member and capable of converting kinetic energy of motion of the operating member to electrical energy. The power manager is connected to the generator and capable of converting electrical energy generated by the generator to an output current. The signal emitter is connected to the power manager and capable of using energy obtained from the output current to send a trigger signal wirelessly.

The alarm device for an MRI system can convert the kinetic energy of motion of the operating member to electrical energy, and use the generated electrical energy to send a trigger signal wirelessly, so does not require an external power supply and has a high level of reliability.

In another exemplary embodiment of the alarm device for an MRI system, the operating member is connected to the body in such a way as to be movable in a first direction and the direction opposite to the first direction. The operating member has a rack part. The rack part has multiple teeth arranged in the first direction. The generator comprises an input gear, an output member and a transducer. The input gear is meshed with the rack part. The input gear is capable of driving the output member to rotate. The transducer is connected to the output member and capable of converting kinetic energy of rotation of the output member to electrical energy. This structure has good stability.

In another exemplary embodiment of the alarm device for an MRI system, the transducer comprises a base plate, a pressure wheel and a first piezoelectric ceramic element. The output member is capable of driving the base plate to rotate. The pressure wheel is rotatably connected to the base plate, with a rotation axis of the pressure wheel being parallel to a rotation axis of the base plate. Two ends of the first piezoelectric ceramic element are fixed relative to the body. As the base plate rotates, the pressure wheel can roll along and press the first piezoelectric ceramic element to generate electrical energy. This structure has good stability.

In another exemplary embodiment of the alarm device for an MRI system, the transducer is provided with multiple pressure wheels and multiple first piezoelectric ceramic elements. The multiple pressure wheels are arranged rotationally around the rotation axis of the base plate. The multiple first piezoelectric ceramic elements are arranged rotationally around the rotation axis of the base plate. The amount of electricity generated is thereby increased.

In another exemplary embodiment of the alarm device for an MRI system, the generator further comprises a ratchet mechanism. A ratchet of the ratchet mechanism is fixedly connected to the output member, and a pawl of the ratchet mechanism is rotatably connected to the base plate. The output member can drive the base plate to rotate in a single direction by means of the ratchet mechanism. The resistance encountered by the operating member when returning to an initial position is thereby reduced.

In another exemplary embodiment of the alarm device for an MRI system, the first piezoelectric ceramic element is a piezoelectric bimorph, a piezoelectric unimorph or a stacked piezoelectric ceramic. Stability is thereby increased.

In another exemplary embodiment of the alarm device for an MRI system, the transducer is a coil, connected to the output member and capable of rotating under the driving action of the output member in order to cut magnetic force lines. This structure is simple, helping to reduce costs.

In another exemplary embodiment of the alarm device for an MRI system, the generator further comprises a transmission assembly. The transmission assembly comprises a first transmission gear and a second transmission gear. The first transmission gear is arranged coaxially with the input gear and fixedly connected thereto. The second transmission gear is meshed with the first transmission gear. The second transmission gear is fixedly connected to the output member. The input gear is capable of driving the output member to rotate by means of the transmission assembly. This can facilitate adjustment of the transmission ratio.

In another exemplary embodiment of the alarm device for an MRI system, the alarm device further comprises a return spring, capable of applying an elastic force to the operating member to drive the operating member to move in the first direction. Operation can thereby be facilitated.

In another exemplary embodiment of the alarm device for an MRI system, the generator comprises a piezoelectric assembly and a pad. The piezoelectric assembly and the pad are stacked in a second direction. The piezoelectric assembly comprises two second piezoelectric ceramic elements and a support ring. The second piezoelectric ceramic element is in the form of a plate and is set perpendicular to the second direction. The two second piezoelectric ceramic elements are arranged in the second direction. The support ring is arranged between the two second piezoelectric ceramic elements and has a central hole running in the second direction. The support ring and the two second piezoelectric ceramic elements together enclose a separating space. The pad is aligned with the separating space in the second direction. The operating member is rotatably connected to the body and has a rotation axis perpendicular to the second direction. The operating member is capable of pressing against the pad in the process of rotating so that the second piezoelectric ceramic element deforms and generates electrical energy. This structure is simple and facilitates manufacture.

In another exemplary embodiment of the alarm device for an MRI system, the generator is provided with multiple piezoelectric assemblies and multiple pads. The multiple piezoelectric assemblies and the multiple pads are stacked alternately in the second direction. The amount of electricity generated is thereby increased.

In another exemplary embodiment of the alarm device for an MRI system, the second piezoelectric ceramic element is a piezoelectric bimorph, a piezoelectric unimorph or a stacked piezoelectric ceramic. Stability is thereby increased.

The present disclosure further provides an alarm system for an MRI system, comprising an alarm device as described above and a receiver. The receiver is capable of receiving the trigger signal and emitting a prompt signal on the basis of the trigger signal. The alarm device of the alarm system for an MRI system can convert the kinetic energy of motion of the operating member to electrical energy, and use the generated electrical energy to send a trigger signal wirelessly, so does not require an external power supply and has a high level of reliability.

In another exemplary embodiment of the alarm system for an MRI system, the alarm system further comprises an alerting device. The alerting device is connected to the receiver and capable of converting the prompt signal to a sound signal or a light signal, in order to attract an operator's attention.

Figure 1:
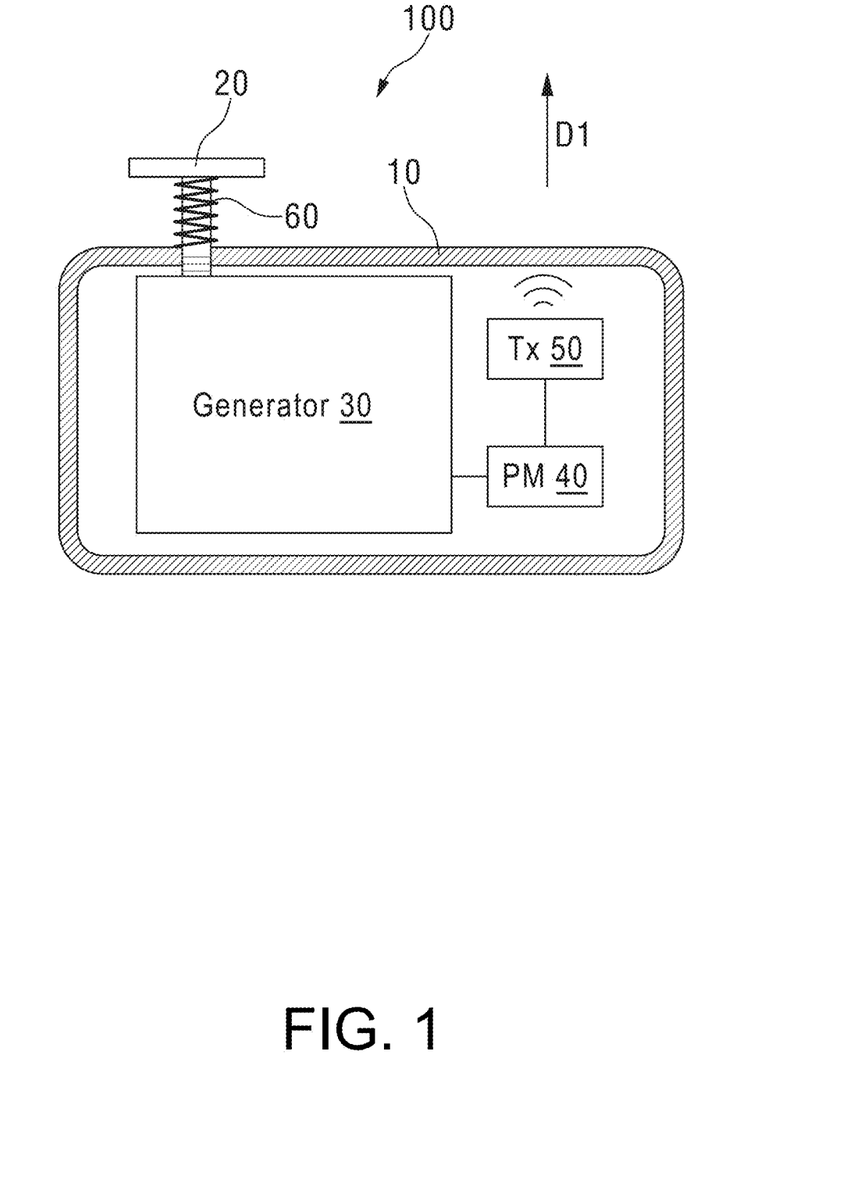
FIG. 1 is a structural schematic drawing of an alarm device for an MRI system according to an exemplary embodiment.

FIG. 1 is a structural schematic drawing of an exemplary embodiment of an alarm device for an MRI system. As shown in FIG. 1, an alarm device 100 for an MRI system comprises a body 10, an operating member 20, a generator 30, a power manager 40, a signal emitter (transmitter) 50 and a return spring 60. In an exemplary embodiment, the alarm device 100 and/or one or more components forming the alarm device 100 (e.g. generator 30, power manager 40, and/or transmitter 50) includes processing circuitry that is configured to perform one or more functions and/or operations of the alarm device 100 (and/or respective component (s) therein).

Figure 2:
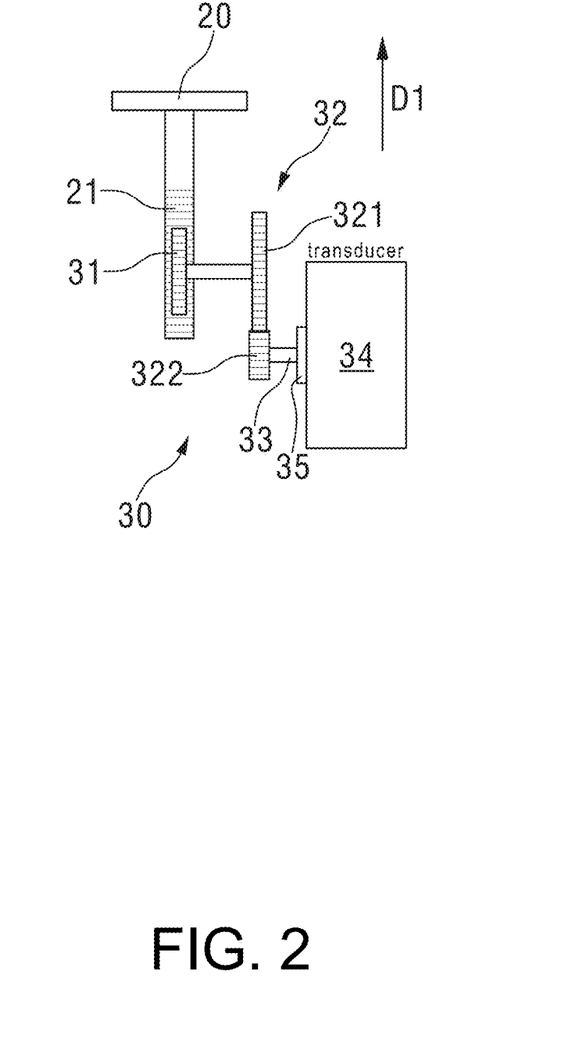
FIG. 2 is a structural schematic drawing illustrating a generator, according to an exemplary embodiment, of the alarm device shown in FIG. 1.

The operating member 20 is movably connected to the body 10. Specifically, in this schematic embodiment, the operating member 20 passes through the body 10 in such a way as to be movable in a first direction D1 and the direction opposite to the first direction D1. The return spring 60 can apply an elastic force to the operating member 20, to drive the operating member 20 to move in the first direction D1. Thus, during use, the user will press the operating member 20 in the direction opposite to the first direction D1, and when it is released, the operating member 20 can move in the first direction D1 under the action of the return spring 60 and thereby return to an initial position. The return spring 60 is for example a compression spring surrounding the operating member 20, and having one end in abutment with the operating member 20 and another end in abutment with the body 10. As shown in FIG. 2, the operating member 20 has a rack part 21. The rack part 21 has multiple teeth arranged in the first direction D1.

The generator 30 is connected to the operating member 20 and can convert kinetic energy of motion of the operating member 20 to electrical energy. Specifically, as shown in FIG. 2, in this schematic embodiment, the generator 30 comprises an input gear 31, a transmission assembly 32, an output member 33 and a transducer 34. The input gear 31 is meshed with the rack part 21, and the input gear 31 can be driven to rotate when the operating member 20 moves in the first direction D1 or the direction opposite to the first direction D1. The transmission assembly 32 comprises a first transmission gear 321 and a second transmission gear 322. The first transmission gear 321 is arranged coaxially with the input gear 31 and fixedly connected thereto; in this schematic embodiment, the two gears are fixedly connected by a shaft rod, but in other schematic embodiments may also be directly connected. The second transmission gear 322 is meshed with the first transmission gear 321. The second transmission gear 322 is fixedly connected to the output member 33. Thus, the input gear 31 can drive the output member 33 to rotate by means of the transmission assembly 32. However, there is no restriction to this. In other schematic embodiments, the input gear 31 may also drive the output member 33 to rotate via another transmission structure or directly.

In an exemplary embodiment, the transmission ratio of the input gear 31 and the transmission assembly 32 may be suitably set according to requirements, e.g. so that the angular velocity of the output member 33 is greater than the angular velocity of the input gear 31, so as to increase the amount of electricity generated.

Figure 3:
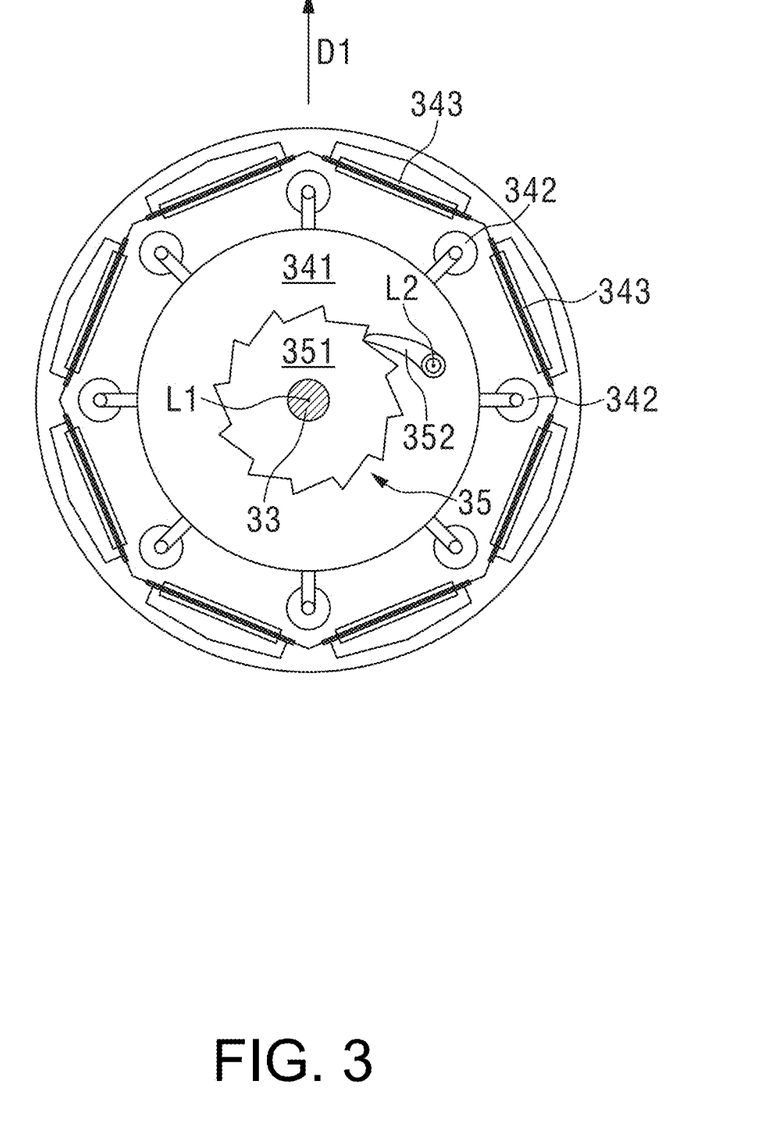
FIG. 3 is a structural schematic drawing illustrating a transducer, according to an exemplary embodiment, of the generator shown in FIG. 2.

The transducer 34 is connected to the output member 33 and can convert kinetic energy of rotation of the output member 33 to electrical energy. Specifically, as shown in FIG. 3, in this exemplary embodiment, the transducer 34 comprises a base plate 341, multiple pressure wheels 342 (only two of which are labelled schematically in FIG. 3), and multiple first piezoelectric ceramic elements 343 (only two of which are labelled schematically in FIG. 3). The first piezoelectric ceramic element 343 is for example a piezoelectric bimorph, a piezoelectric unimorph or a stacked piezoelectric ceramic, but there is no restriction to this. The multiple first piezoelectric ceramic elements 343 are for example connected in series, but there is no restriction to this.

The output member 33 can drive the base plate 341 to rotate relative to the body 10; in FIG. 3, a rotation axis L1 of the base plate 341 is perpendicular to the plane of the figure. The pressure wheels 342 are rotatably connected to the base plate 341, and rotation axes of the pressure wheels 342 are parallel to the rotation axis L1 of the base plate 341. The multiple pressure wheels 342 are arranged rotationally around the rotation axis L1 of the base plate 341, i.e. one pressure wheel 342 reaches the position and angle of another pressure wheel 342 by rotating through an angle around the rotation axis L1 of the base plate 341. Two ends of each first piezoelectric ceramic element 343 are fixed relative to the body 10. The multiple first piezoelectric ceramic elements 343 are arranged rotationally around the rotation axis L1 of the base plate 341, i.e. one first piezoelectric ceramic element 343 reaches the position and angle of another first piezoelectric ceramic element 343 by rotating through an angle around the rotation axis L1 of the base plate 341. As the base plate 341 rotates, the pressure wheels 342 can roll along and press the first piezoelectric ceramic elements 343 in order to generate electrical energy by the piezoelectric effect. In other schematic embodiments, the number of pressure wheels 342 and the number of first piezoelectric ceramic elements 343 may be adjusted as required, e.g. may both be set to one.

As shown in FIGS. 2 and 3, in this exemplary embodiment, the generator 30 further comprises a ratchet mechanism 35. The transducer 34 is connected to the output member 33 via the ratchet mechanism 35. Specifically, as shown in FIG. 3, the ratchet mechanism 35 comprises a ratchet 351 and a pawl 352. The ratchet 351 is fixedly connected to the output member 33, wherein the rotation axes of the output member 33, base plate 341 and ratchet 351 overlap. The pawl 352 is rotatably connected to the base plate 341 and a rotation axis L2 of the pawl 352 is parallel to the rotation axis L1 of the base plate 341. Thus, the output member 33 can drive the base plate 341 to rotate in a single direction by means of the ratchet mechanism 35. Specifically, when the operating member 20 moves in the direction opposite to the first direction D1, the operating member 20 drives the ratchet 351 shown in FIG. 3 to rotate clockwise by means of the input gear 31, the transmission assembly 32 and the output member 33; the pawl is jammed in a trough between teeth of the ratchet 351, so the ratchet 351 drives the base plate 341 to rotate clockwise by means of the pawl 352. When the operating member 20 moves in the first direction D1, the operating member 20 drives the ratchet 351 shown in FIG. 3 to rotate anticlockwise by means of the input gear 31, the transmission assembly 32 and the output member 33; pushed by tooth faces of the ratchet 351, the pawl 352 rotates relative to the base plate 341, and the base plate 341 does not rotate. Because the base plate 341 does not rotate when the operating member 20 moves in the first direction D1, there is little resistance to the movement of the operating member 20, thus facilitating its return to the initial position. However, there is no restriction to this. In other exemplary embodiments, it is also possible for no ratchet mechanism 35 to be provided, and the output member 33 is configured to drive the base plate 341 to rotate directly.

As shown in FIG. 1, the power manager 40 is connected to the generator 30, and can convert the electrical energy generated by the generator 30 to an output current. Specifically, in this exemplary embodiment, the power manager 40 is connected to the first piezoelectric ceramic elements 343. The power manager 40 can for example subject the electrical energy generated by the generator 30 to rectification, storage and voltage stabilization before outputting an output current. The signal emitter 50 is connected to the power manager 40, and can use energy obtained from the output current to send a trigger signal wirelessly.

The alarm device for an MRI system can convert the kinetic energy of motion of the operating member to electrical energy, and use the generated electrical energy to send a trigger signal wirelessly, so does not require an external power supply and has a high level of reliability.

In the exemplary embodiment described above, the pressure wheels 342 roll along and press the first piezoelectric ceramic elements 343 and the transducer 34 thereby generates electrical energy, but there is no restriction to this. In other exemplary embodiments, the transducer 34 may also be configured as a coil, which is connected to the output member 33 and can rotate under the driving action of the output member 33 in order to cut magnetic force lines, so as to generate electrical energy. The magnetic force lines are for example magnetic force lines of the main magnetic field of the MRI system.

Figure 4:
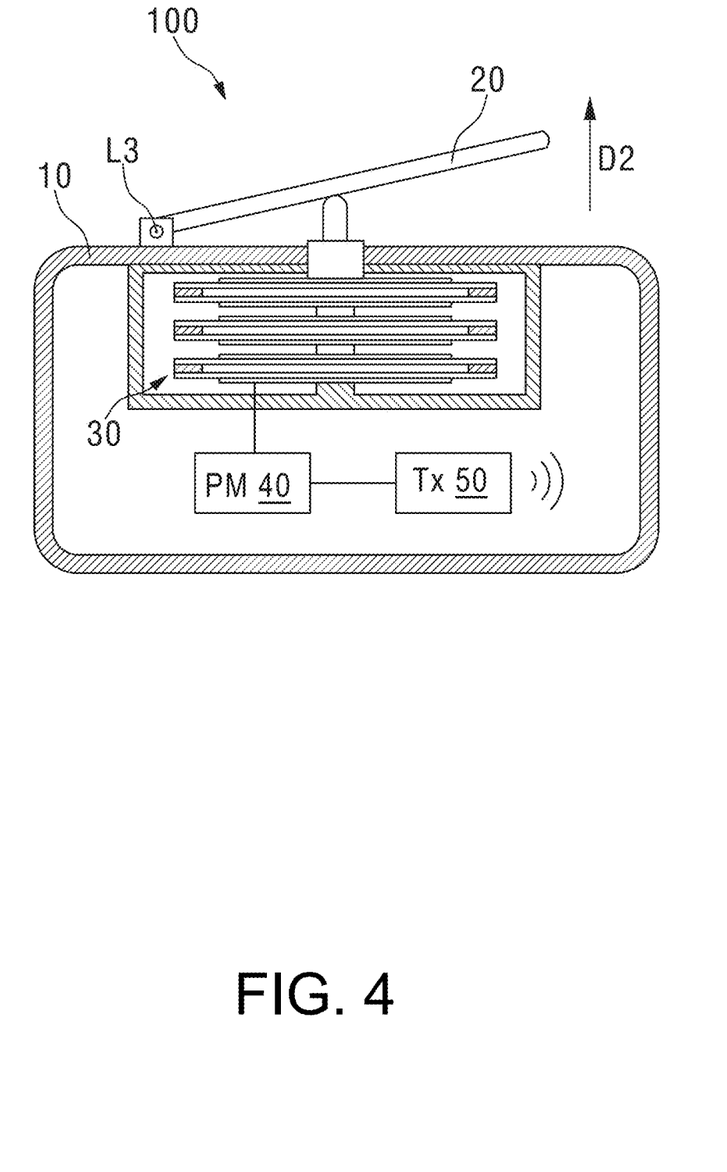
FIG. 4 is a structural schematic drawing of an alarm device for an MRI system according to an exemplary embodiment.
Figure 5:
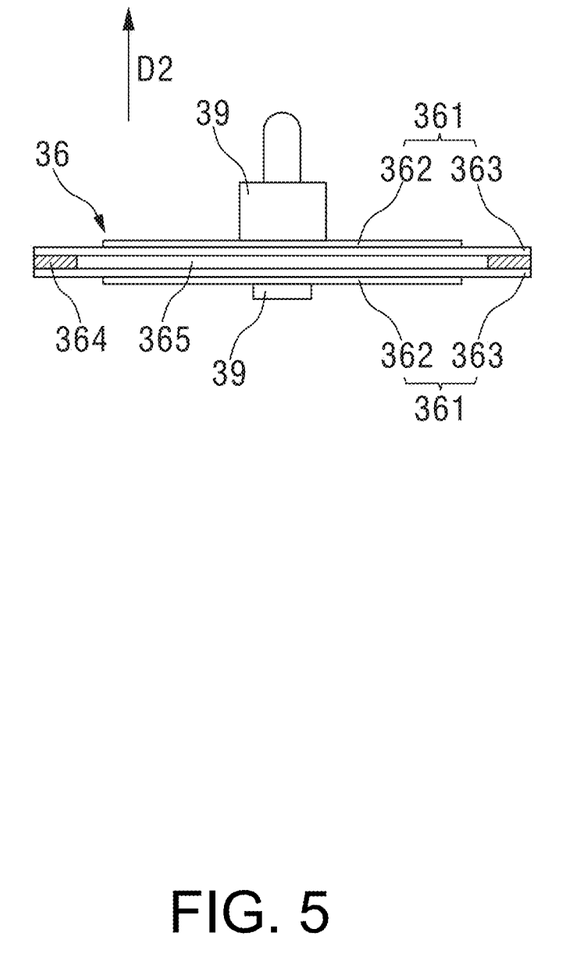
FIG. 5 is a partial structural schematic drawing illustrating the generator, according to an exemplary embodiment, of the alarm device shown in FIG. 4.

FIG. 4 is a structural schematic drawing of another exemplary embodiment of an alarm device for an MRI system. The features of the alarm device in this exemplary embodiment that are different from the alarm device shown in FIG. 1 are the generator 30 and the operating member 20; identical features are not described again here. FIG. 5 is a partial structural schematic drawing illustrating the generator of the alarm device shown in FIG. 4. As shown in FIGS. 4 and 5, in this exemplary embodiment, the generator 30 comprises multiple piezoelectric assemblies 36 and multiple pads 39. The multiple piezoelectric assemblies 36 and multiple pads 39 are stacked alternately in a second direction D2. The multiple pads 39 may be configured to have different shapes as required.

As shown in FIG. 5, each piezoelectric assembly 36 comprises two second piezoelectric ceramic elements 361 and one support ring 364. The second piezoelectric ceramic element 361 is in the form of a plate, and is set perpendicular to the second direction D2. The two second piezoelectric ceramic elements 361 are arranged in the second direction D2. The support ring 364 is positioned between the two second piezoelectric ceramic elements 361, and has a central hole running in the second direction D2. The support ring 364 is for example a round ring, and an axis thereof is parallel to the second direction D2. The support ring 364 and the two second piezoelectric ceramic elements 361 together enclose a separating space 365. The pad 39 is aligned with the separating space 365 in the second direction D2.

As shown in FIG. 4, one end of the operating member 20 is rotatably connected to the body 10, and a rotation axis L3 of the operating member 20 is perpendicular to the second direction D2; in FIG. 4, the rotation axis L3 of the operating member 20 is perpendicular to the plane of the figure. In the process of rotating, the operating member 20 can press against the outermost pad 39 so that the second piezoelectric ceramic elements 361 deform and generate electrical energy by the piezoelectric effect. The second piezoelectric ceramic elements 361 of the multiple piezoelectric assemblies 36 are for example connected in series. In this exemplary embodiment, the power manager 40 is connected to the second piezoelectric ceramic elements 361.

In this exemplary embodiment, the generator 30 comprises multiple piezoelectric assemblies 36, to help increase the amount of electricity generated. However, there is no restriction to this. In other exemplary embodiments, the number of piezoelectric assemblies 36 and the number of pads 39 may be adjusted as required, e.g. may both be set to one.

As shown in FIG. 5, in an exemplary embodiment, the second piezoelectric ceramic element 361 comprises a piezoelectric ceramic plate 362 and a metal pole plate 363 which are stacked one on top of the other. That is to say, the second piezoelectric ceramic element 361 is a piezoelectric unimorph. The side of the second piezoelectric ceramic element 361 on which the metal pole plate 363 is provided faces the support ring 364. In another exemplary embodiment, the second piezoelectric ceramic element 361 may be a piezoelectric bimorph or a stacked piezoelectric ceramic.

Figure 6:
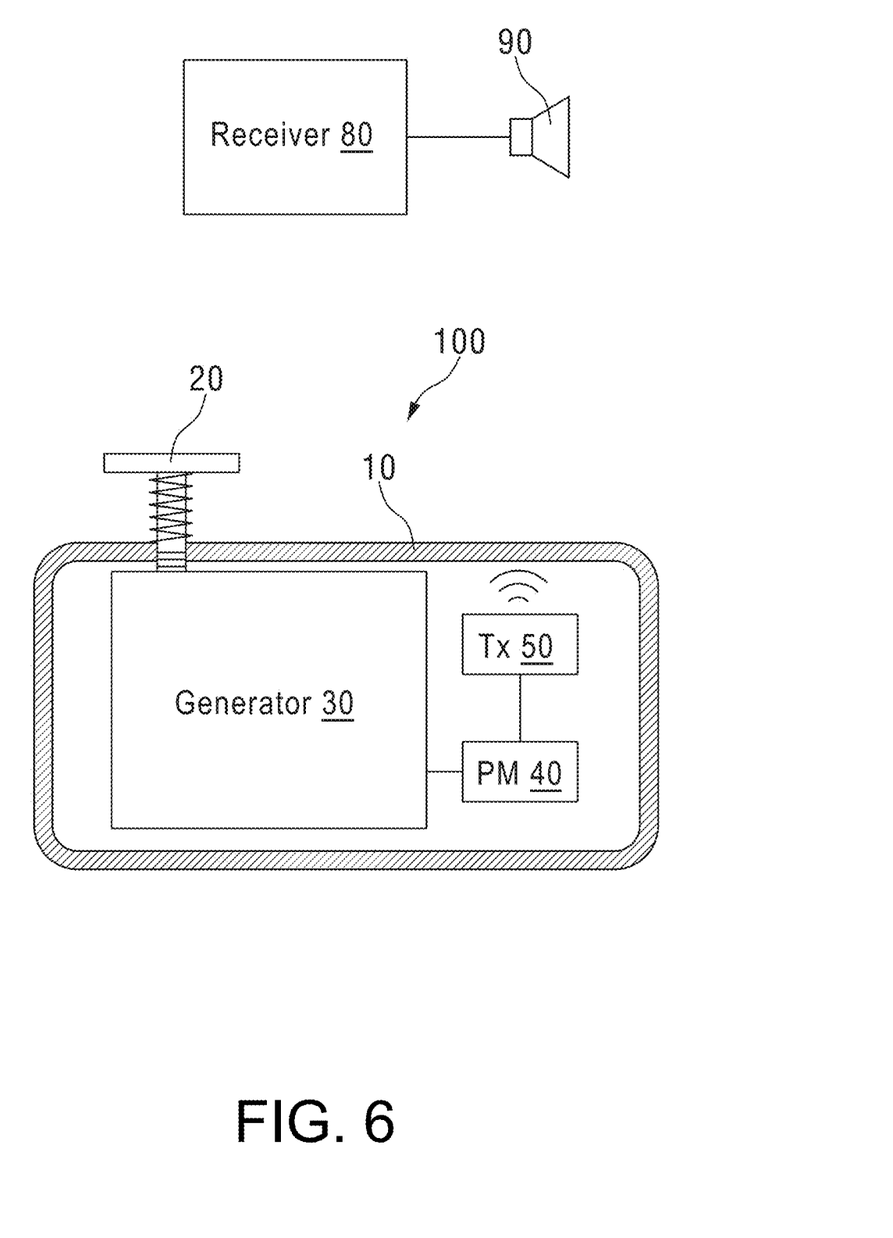
FIG. 6 is a structural schematic drawing of an alarm system for an MRI system according to an exemplary embodiment.

The present disclosure also provides an alarm system for an MRI system. FIG. 6 is a structural schematic drawing of an exemplary embodiment of an alarm system for an MRI system. As shown in FIG. 6, the alarm system comprises an alarm device as shown in FIG. 1, a receiver 80 and an alerting device 90. The receiver 80 can receive a trigger signal and emit a prompt signal on the basis of the trigger signal. The alerting device 90 is connected to the receiver 80, and can convert the prompt signal to a sound signal or a light signal. In an exemplary embodiment, the alerting device 90 is a speaker, light, vibrator, display, and/or other output device configured to generate an alert and/or notification as would be understood by one or ordinary skill in the art. In an exemplary embodiment, the receiver 80 and/or alerting device 90 includes processing circuitry that is configured to perform one or more respective functions and/or operations of the receiver 80 and/or alerting device 90.

Figure 7:
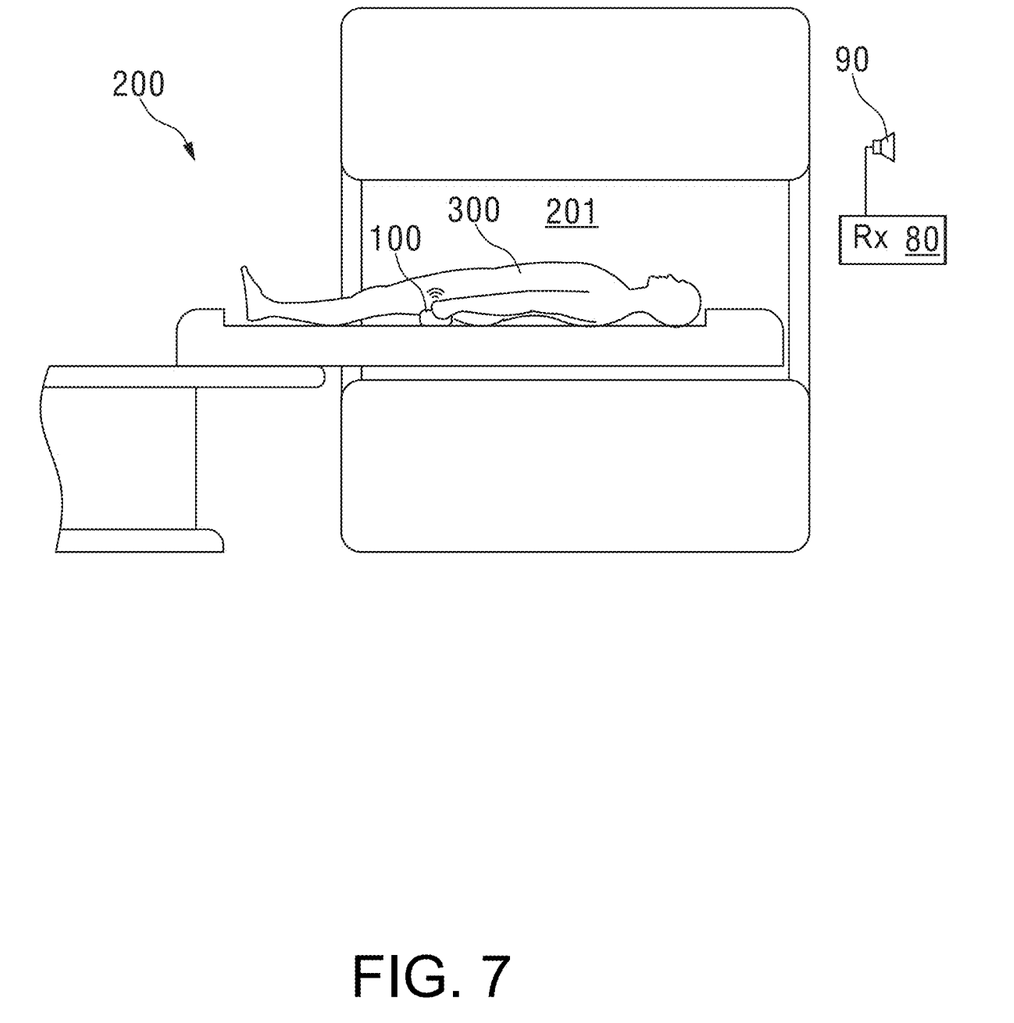
FIG. 7 is a schematic drawing illustrating an alarm system for an MRI system according to an exemplary embodiment.

FIG. 7 is a schematic drawing illustrating a schematic scenario of use of an alarm system for an MRI system, and is not intended to limit the scope of the present disclosure. As shown in FIG. 7, when the alarm system is used, an examination subject 300 holding the alarm device 100 is located in a detection region 201 of an MRI system 200 to undergo a magnetic resonance examination. Although omitted for brevity, the MRI system 200 may include an MR scanner and a controller that controls the MR scanner. The controller may be implemented within the MR scanner and/or externally located and connected thereto. When the examination subject has an alarm demand, the examination subject presses the operating member 20, so that the alarm device 100 emits a trigger signal. The receiver 80 receives the trigger signal and emits a prompt signal on the basis of the trigger signal. The alerting device 90 converts the prompt signal to a sound signal or a light signal, in order to attract the operator's attention. In other schematic embodiments, the alarm device 100 may also be the alarm device shown in FIG. 4.

The alarm device of the alarm system for an MRI system can convert the kinetic energy of motion of the operating member to electrical energy, and use the generated electrical energy to send a trigger signal wirelessly, so does not require an external power supply and has a high level of reliability.

It should be understood that although the description herein is based on various embodiments, it is by no means the case that each embodiment contains just one independent technical solution. Such a method of presentation is adopted herein purely for the sake of clarity. Those skilled in the art should consider the description in its entirety. The technical solutions in the various embodiments could also be suitably combined to form other embodiments understandable to those skilled in the art.

The series of detailed explanations set out above are merely particular explanations of feasible embodiments of the present disclosure, which are not intended to limit the scope of protection thereof. All equivalent embodiments or changes made without departing from the artistic spirit of the present disclosure, such as combinations, divisions or repetitions of features, shall be included in the scope of protection of the present disclosure.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

As used herein, "schematic" means "serving as an instance, example or illustration." No drawing or embodiment described herein as "schematic" should be interpreted as a more preferred or more advantageous technical solution.

As used herein, "first" and "second", etc. do not indicate order or degree of importance, etc., merely being used to indicate a distinction between parts, to facilitate document descriptions.

To make the drawings appear uncluttered, only those parts relevant to the present disclosure are shown schematically in the drawings; they do not represent the actual structure thereof as a product.

REFERENCE LIST 10 body
20 operating member
21 rack part
30 generator
31 input gear
32 transmission assembly
321 first transmission gear
322 second transmission gear
33 output member
34 transducer
341 base plate
342 pressure wheel
343 first piezoelectric ceramic element
35 ratchet mechanism
351 ratchet
352 pawl
36 piezoelectric assembly
361 second piezoelectric ceramic element
362 piezoelectric ceramic plate
363 metal pole plate
364 support ring
365 separating space
39 pad
40 power manager
50 signal emitter (transmitter, Tx)
60 return spring
80 receiver
90 alerting device
100 alarm device
200 MRI system
201 detection region
300 examination subject
D1 first direction
D2 second direction
L1 rotation axis of base plate
L2 rotation axis of pawl
L3 rotation axis of operating member

The invention claimed is:

1. An alarm device for an MRI system, comprising:
a body;
an operating member movably connected to the body, the operating member being movable in a first direction and a direction opposite to the first direction, wherein the operating member includes a rack part having multiple teeth arranged in the first direction;
a generator connected to the operating member and configured to convert kinetic energy of motion of the operating member to electrical energy, the generator including:
an input gear meshed with the rack part;
an output member, the input gear being configured to drive the output member to rotate; and a transducer connected to the output member and configured to convert kinetic energy of rotation of the output member to electrical energy;

a power manager connected to the generator and configured to convert electrical energy generated by the generator to an output current; and a signal emitter connected to the power manager and configured to wirelessly send a trigger signal based on the electrical energy obtained from the output current.

2. The alarm device as claimed in claim 1, wherein the transducer comprises:

a base plate, the output member being configured to drive the base plate to rotate, a pressure wheel rotatably connected to the base plate, a rotation axis of the pressure wheel being parallel to a rotation axis of the base plate, and a first piezoelectric ceramic element, two ends thereof being fixed relative to the body, wherein, as the base plate rotates, the pressure wheel is configured to roll along and press the first piezoelectric ceramic element to generate electrical energy.

3. The alarm device as claimed in claim 2, wherein the transducer comprises multiple of the pressure wheels and multiple of the first piezoelectric ceramic elements, the multiple pressure wheels being arranged rotationally around the rotation axis of the base plate and the multiple first piezoelectric ceramic elements being arranged rotationally around the rotation axis of the base plate.

4. The alarm device as claimed in claim 2, wherein the generator further comprises a ratchet mechanism including: a ratchet that is fixedly connected to the output member, and a pawl that is rotatably connected to the base plate, where the output member is configured to drive the base plate to rotate in a single direction using the ratchet mechanism.

5. The alarm device as claimed in claim 2, wherein the first piezoelectric ceramic element is a piezoelectric bimorph, a piezoelectric unimorph, or a stacked piezoelectric ceramic.

6. The alarm device as claimed in claim 1, wherein the transducer is a coil connected to the output member and configured to rotate under a driving action of the output member to cut magnetic force lines.

7. The alarm device as claimed in claim 1, wherein the generator further comprises a transmission assembly including:

a first transmission gear arranged coaxially with the input gear and fixedly connected thereto, and a second transmission gear meshed with the first transmission gear, the second transmission gear being fixedly connected to the output member, wherein the input gear is configured to drive the output member to rotate using the transmission assembly.

8. The alarm device as claimed in claim 1, wherein the alarm device further comprises a return spring configured to apply an elastic force to the operating member to drive the operating member to move in the first direction.

9. The alarm device as claimed in claim 1, wherein the generator comprises a piezoelectric assembly and a pad, the piezoelectric assembly and the pad being stacked in the first direction, and the piezoelectric assembly comprising:

two second piezoelectric ceramic elements, the two second piezoelectric ceramic elements being in a form of a plate and are set perpendicular to the first direction, and the two second piezoelectric ceramic elements being arranged in the first direction; and a support ring arranged between the two second piezoelectric ceramic elements and having a central hole running in the first direction, the support ring and the two second piezoelectric ceramic elements together enclosing a separating space, and the pad being aligned with the separating space in the first direction, wherein the operating member is rotatably connected to the body and includes a rotation axis perpendicular to the first direction, the operating member being configured to press against the pad while rotating to cause the second piezoelectric ceramic element to deform and generate electrical energy.

10. The alarm device as claimed in claim 9, wherein the generator comprises multiple of the piezoelectric assemblies and multiple of the pads, the multiple piezoelectric assemblies and the multiple pads being stacked alternately in the first direction.

11. The alarm device as claimed in claim 9, wherein the second piezoelectric ceramic element is a piezoelectric bimorph, a piezoelectric unimorph, or a stacked piezoelectric ceramic.

12. An alarm system for an MRI system, comprising:
an alarm device including:
a body;
an operating member movably connected to the body, the operating member being movable in a first direction and a direction opposite to the first direction, wherein the operating member includes a rack part having multiple teeth arranged in the first direction;

a generator connected to the operating member and configured to convert kinetic energy of motion of the operating member to electrical energy, the generator including:

an input gear meshed with the rack part;

an output member, the input gear being configured to drive the output member to rotate; and a transducer connected to the output member and configured to convert kinetic energy of rotation of the output member to electrical energy;

a power manager connected to the generator and configured to convert electrical energy generated by the generator to an output current; and a signal emitter connected to the power manager and configured to wirelessly send a trigger signal based on the electrical energy obtained from the output current; and a receiver configured to receive the trigger signal and emit a prompt signal based on the trigger signal.

13. The alarm system as claimed in claim 12, wherein the alarm system further comprises an alerting device connected to the receiver and configured to convert the prompt signal to an audible signal and/or a visible signal.

14. The alarm system as claimed in claim 13, wherein the alerting device comprises a speaker, and/or a light or display.

15. An alarm device for an MRI system, comprising:
a body;
an operating member movably connected to the body;
a generator connected to the operating member and configured to convert kinetic energy of motion of the operating member to electrical energy, the generator including a piezoelectric assembly and a pad, the piezoelectric assembly and the pad being stacked in a first direction, and the piezoelectric assembly comprising:

two second piezoelectric ceramic elements, the two second piezoelectric ceramic elements being in a form of a plate and are set perpendicular to the first direction, and the two second piezoelectric ceramic elements being arranged in the first direction; and a support ring arranged between the two second piezoelectric ceramic elements and having a central hole running in the first direction, the support ring and the two second piezoelectric ceramic elements together enclosing a separating space, and the pad being aligned with the separating space in the first direction;

a power manager connected to the generator and configured to convert electrical energy generated by the generator to an output current; and a signal emitter connected to the power manager and configured to wirelessly send a trigger signal based on the electrical energy obtained from the output current, wherein the operating member is rotatably connected to the body and includes a rotation axis perpendicular to the first direction, the operating member being configured to press against the pad while rotating to cause the second piezoelectric ceramic element to deform and generate electrical energy.

16. An alarm system for an MRI system, comprising:
the alarm device according to claim 15; and
a receiver configured to receive the trigger signal and emit a prompt signal based on the trigger signal.

* * * * *